United States Patent
Zook et al.

(10) Patent No.: US 7,304,069 B2
(45) Date of Patent: Dec. 4, 2007

(54) HYDRATE OF N-METHYL-N-(3-{3-[2-THIENYLCARBONYL]-PYRAZOL-[1,5α]-PYRIMIDIN-7-YL}PHENYL) ACETAMIDE AND PROCESSES AND METHODS RELATED THERETO

(75) Inventors: Scott E Zook, San Diego, CA (US); Donald Hettinger, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 13 days.

(21) Appl. No.: 11/252,194

(22) Filed: Oct. 17, 2005

(65) Prior Publication Data

US 2006/0116387 A1 Jun. 1, 2006

Related U.S. Application Data

(60) Provisional application No. 60/620,014, filed on Oct. 18, 2004.

(51) Int. Cl.
*C07D 487/04* (2006.01)
*A61K 31/519* (2006.01)
*A61P 25/20* (2006.01)

(52) U.S. Cl. .................................... 514/259.3; 544/281

(58) Field of Classification Search ................. 544/281; 514/259.3
See application file for complete search history.

(56) References Cited

U.S. PATENT DOCUMENTS

| 6,384,221 | B1 | 5/2002 | Thiele et al. ................ 544/281 |
| 6,399,621 | B1 | 6/2002 | Dusza et al. ................. 514/258 |
| 6,472,528 | B1 | 10/2002 | Gross et al. ................. 544/281 |
| 6,485,746 | B1 | 11/2002 | Campbell et al. ............ 424/468 |
| 6,544,999 | B2 | 4/2003 | Thiele et al. ............. 514/259.3 |
| 6,903,106 | B2 | 6/2005 | Zook et al. .............. 514/259.3 |
| 2005/0267176 | A1* | 12/2005 | Barberich .................... 514/373 |

FOREIGN PATENT DOCUMENTS

WO 2004/018476 3/2004

* cited by examiner

*Primary Examiner*—Brenda L. Coleman
*Assistant Examiner*—Susanna Moore
(74) *Attorney, Agent, or Firm*—Seed IP Law Group PLLC

(57) ABSTRACT

A novel hydrate form of N-methyl-N-(3-{3-[2-thienylcarbonyl]-pyrazol-[1,5-α]-pyrimidin-7-yl}phenyl)acetamide ("Compound No. 1") and processes related to the use thereof in the synthesis of a polymorphic form of Compound No. 1.

10 Claims, 3 Drawing Sheets

HYDRATE OF N-METHYL-N-(3-{3-[2-THIENYLCARBONYL]-PYRAZOL-[1,5α]-PYRIMIDIN-7-YL}PHENYL) ACETAMIDE AND PROCESSES AND METHODS RELATED THERETO

CROSS-REFERENCE TO RELATED APPLICATION

This application claims the benefit under 35 U.S.C. § 119(e) of U.S. Provisional Application No. 60/620,014 filed Oct. 18, 2004, which is hereby incorporated by reference in its entirety.

BACKGROUND OF THE INVENTION

1. Field of the Invention

This invention is generally directed to a hydrate of N-methyl-N-(3-{3-[2-thienylcarbonyl]-pyrazol-[1,5-α]-pyrimidin-7-yl}phenyl)acetamide ("Compound No. 1") and to processes related to the use thereof in the synthesis of a polymorphic form of Compound No. 1.

2. Description of the Related Art

Recently, a new class of agents has undergone development for the treatment of insomnia. These agents are non-benzodiazepine compounds, which bind selectively to a specific receptor subtype of the benzodiazepine receptor. This receptor selectivity is thought to be the mechanism by which these compounds are able to exert a robust hypnotic effect, while also demonstrating an improved safety profile relative to the non-selective, benzodiazepine class of agents. The first of these agents to be approved by the United States Food and Drug Administration (FDA) for marketing in the United States was Ambien® (zolpidem tartrate), which is based on the imidazopyridine backbone (see U.S. Pat. Nos. 4,382,938 and 4,460,592). In addition to Ambien®, another compound known as Sonata® (zaleplon), which is a pyrazolopyrimidine-based compound, has received FDA approval (see U.S. Pat. No. 4,626,538). Recently, the FDA approved Lunesta™ (see U.S. Pat. No. 6,444,673) as a prescription sleep aid. Other non-benzodiazepine compounds and/or methods for making or using the same have also been reported (see, e.g., U.S. Pat. Nos. 4,794,185, 4,808,594, 4,847,256, 5,714,607, 4,654,347 and 5,891,891).

While significant advances have been made in this field, there is still a need in the art for compounds that are effective as sedative or hypnotic agents generally, particularly in the context of treating insomnia. One such compound is N-methyl-N-(3-{3-[2-thienylcarbonyl]-pyrazol-[1,5-α]-pyrimidin-7-yl}phenyl)acetamide (Compound No. 1), which is also known by the generic name "Indiplon". Compound No. 1 is disclosed in U.S. Pat. No. 6,399,621 and has the following chemical structure:

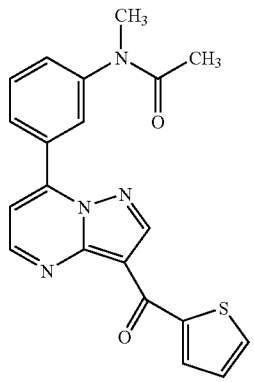

In addition, U.S. Pat. Nos. 6,472,528 and 6,485,746 are directed to the synthesis of Compound No. 1 and to a controlled release pharmaceutical composition containing Compound No. 1, respectively. Furthermore, U.S. Pat. Nos. 6,384,221 and 6,544,999 are directed to certain polymorphic forms of Compound No. 1 (i.e., Forms I and II), while U.S. Pat. No. 6,903,106 is directed to an additional polymorphic form (i.e., Form III) of Compound No. 1.

While Compound No. 1 has proven particularly promising for the treatment of insomnia, improvements related to the preparation of Compound No. 1 are still desired.

BRIEF SUMMARY OF THE INVENTION

This invention is generally directed to a hydrate form of N-methyl-N-(3-{3-[2-thienylcarbonyl]-pyrazol-[1,5-α]-pyrimidin-7-yl}phenyl)acetamide ("Compound No. 1") and to processes related to the use thereof in the synthesis of a polymorphic form of Compound No. 1; namely, polymorph Form I of Compound No. 1 (hereinafter "polymorph Form I"). This hydrate of Compound No. 1 converts to polymorph Form I upon drying (e.g., heating), and is referred to herein as the "Compound No. 1 hydrate."

Accordingly, in one embodiment, a novel Compound No. 1 hydrate is disclosed. In a further embodiment, a Compound No. 1 hydrate is disclosed having a broad endotherm at about 40-90° C. and an endotherm peak at about 193° C., as measured by a TA 2920 Modulated Differential Scanning Calorimeter (DSC) at a scan rate of 10° C. per minute. In a further embodiment, the novel Compound No. 1 hydrate exhibits an X-ray powder diffraction having characteristic peaks expressed in degrees 2θθ+/−0.2° θ at 6.1 and 17.2. In a still further embodiment, the X-ray powder diffraction exhibits further characteristic peaks at 20.7, 25 and/or 26.3.

In another embodiment, a method is disclosed for making polymorph Form I comprising the step of drying the Compound No. 1 hydrate. Such drying may occur at, for example, temperatures ranging from about room temperature up to about 90° C. for a period of time ranging from hours to days. In this context, vacuum drying may be employed.

In still a further embodiment, a method is disclosed for making the Compound No. 1 hydrate comprising the steps of combining (a) an acetic acid solution comprising Compound No. 1 and acetic acid with (b) an aqueous solution comprising water and one or more optional cosolvents to form a hydrate of Compound No. 1. In a further embodiment the method includes collecting the Compound No. 1 hydrate as the precipitate. In this method, a variety of mixing and reaction conditions may be employed, as disclosed in greater detail below.

These and other aspects of this invention will be apparent upon reference to the following detailed description and attached figures. To that end, certain patent and other documents are cited herein to more specifically set forth various aspects of this invention. Each of these documents is hereby incorporated by reference in its entirety.

DETAILED DESCRIPTION OF THE INVENTION

As mentioned above, this invention is generally directed to a novel hydrate form of N-methyl-N-(3-{3-[2-thienylcarbonyl]-pyrazol-[1,5-α]-pyrimidin-7-yl}phenyl)-acetamide ("Compound No. 1") and to processes related to the use thereof in the synthesis of a polymorphic form of Compound No. 1; namely, polymorph Form I of Compound No. 1. For purpose of convenience, the novel hydrate form of Compound No. 1, which may be used in the preparation polymorph Form I of Compound No. 1, is hereinafter referred to as the "Compound No. 1 hydrate," while polymorph Form I of Compound No. 1 is hereinafter referred to as "polymorph Form I".

Polymorph Form I has a predominant endotherm peak at about 193° C. (as measured by a TA 2920 Modulated Differential Scanning Calorimeter (DSC) at a scan rate of 10° C. per minute). This polymorph, along with another polymorphic form of Compound No. 1 (i.e., Form II) is the subject matter of U.S. Pat. Nos. 6,384,221 and 6,544,999. More recently, an additional polymorphic form of Compound No. 1, referred to as "polymorph Form III," has been identified and is the subject of U.S. Pat. No. 6,903,106 and PCT Application No. PCT/US03/26870 (WO 2004/018476A1).

Subsequent to the synthesis and identification of polymorph Form III, it has become difficult to continue to synthesize polymorph Form I in large quantities due to the formation of polymorph Form III. Surprisingly, the present inventors have discovered that, by the procedures disclosed herein, the Compound No. 1 hydrate exclusively converts upon drying to polymorph Form I at commercial scale and on a reproducible basis. In addition, the Compound No. 1 hydrate may be isolated and stored under appropriate conditions for later production of polymorph Form I.

Figure 1:
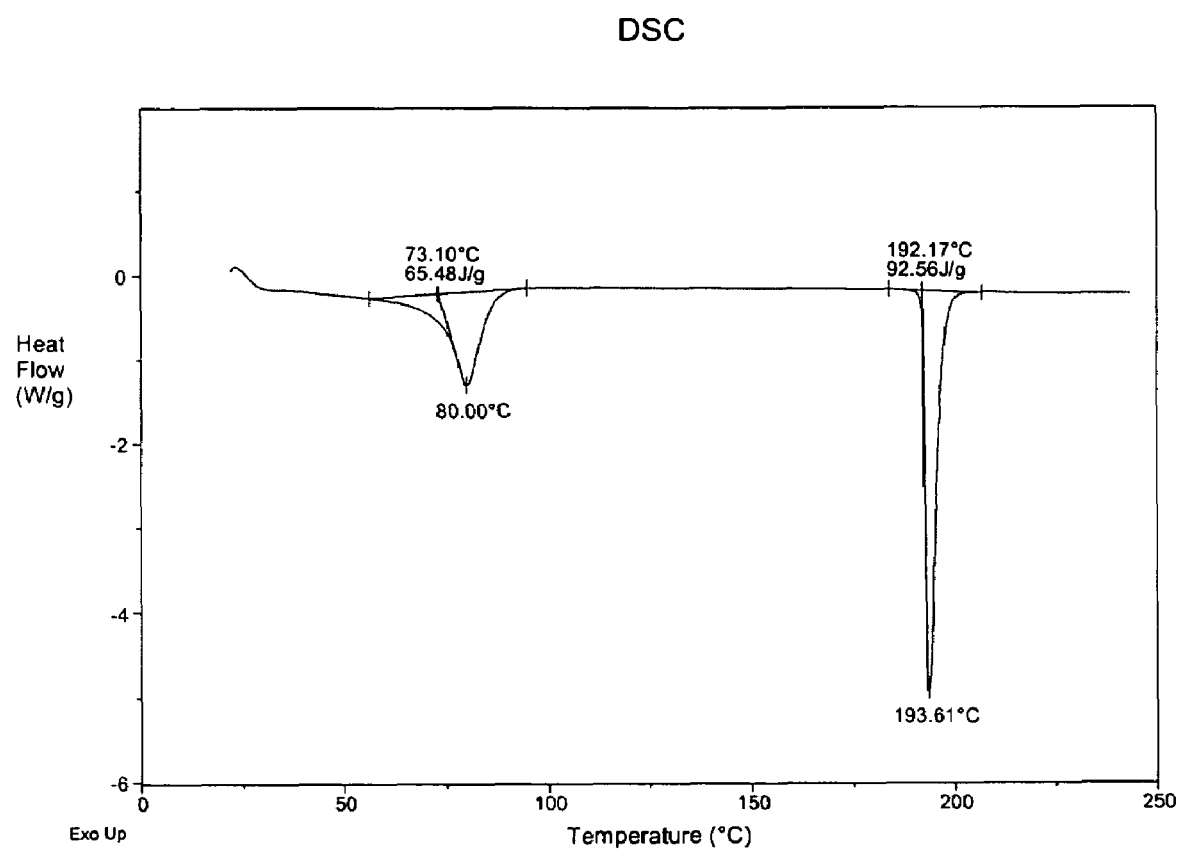
FIG. 1 is a Differential Scanning Calorimetry (DSC) thermogram of the Compound No. 1 hydrate.

The Compound No. 1 hydrate may be characterized by, for example, melting point or DSC endotherm and/or X-Ray powder diffraction spectrometry. As shown in FIG. 1, the Compound No. 1 hydrate exhibits a predominant broad endotherm peak at about 80° C. and a second endotherm peak at about 193° C. as measured by a TA 2920 (TA Instruments, New Castle, Del.) Modulated Differential Scanning Calorimeter (DSC) at a scan rate of 10° C. per minute with an Indium standard. In this regard, it should be understood that the endotherm measured by a particular differential scanning calorimeter is dependent upon a number of factors, including the rate of heating (i.e., scan rate), the calibration standard utilized, instrument calibration, relative humidity, and upon the chemical purity of the sample being tested.

Figure 2:
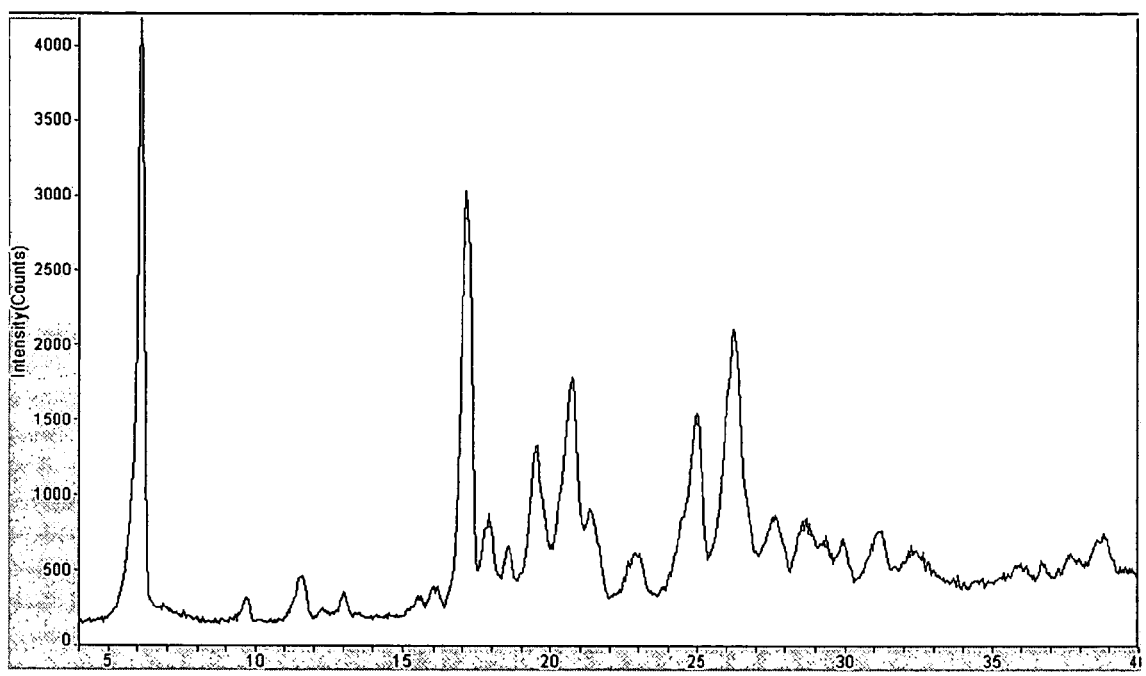
FIG. 2 is an X-ray powder diffraction spectrum of the Compound No. 1 hydrate.

The X-Ray powder diffraction spectrum for the Compound No. 1 hydrate is presented in FIG. 2, and is set forth in tabular form in Table 1 below. The X-Ray powder diffraction was measured using a Rigaku Miniflex X-Ray Diffractometer equipped with graphite monochromator and a Cu (λ=1.54 Angstrom) X-ray source operated at 30 kV, 15 mA. The sample was analyzed using the following instrument parameters: measuring range=4-40° 2θ; step width=0.0500°; and a 2.5°/min scan speed.

TABLE 1

X-Ray Powder Diffraction Spectral Lines

| 2-θ° | d value | Intensity | Intensity % |
|---|---|---|---|
| 6.099 | 14.4802 | 4020 | 100.0 |
| 9.657 | 9.1507 | 165 | 4.1 |
| 11.592 | 7.6275 | 278 | 6.9 |
| 13.001 | 6.8037 | 166 | 4.1 |
| 16.008 | 5.5318 | 122 | 3.0 |
| 17.151 | 5.1657 | 2656 | 66.1 |
| 17.903 | 4.9505 | 304 | 7.6 |
| 18.561 | 4.7765 | 170 | 4.2 |
| 19.586 | 4.5287 | 728 | 18.1 |
| 20.749 | 4.2773 | 1176 | 29.3 |
| 21.353 | 4.1578 | 580 | 14.4 |
| 22.902 | 3.8799 | 275 | 6.8 |
| 24.999 | 3.5590 | 941 | 23.4 |
| 26.253 | 3.3918 | 1464 | 36.4 |
| 27.699 | 3.2179 | 276 | 6.9 |
| 28.749 | 3.1027 | 278 | 6.9 |
| 29.393 | 3.0362 | 191 | 4.8 |
| 29.959 | 2.9801 | 174 | 4.3 |
| 31.289 | 2.8564 | 266 | 6.6 |
| 32.304 | 2.7690 | 170 | 4.2 |
| 36.035 | 2.4903 | 109 | 2.7 |
| 36.773 | 2.4420 | 107 | 2.7 |
| 37.740 | 2.3816 | 103 | 2.6 |
| 38.853 | 2.3159 | 221 | 5.5 |

Table 2 lists the spectra lines generally having the greatest intensities.

TABLE 2

X-Ray Powder Diffraction Spectral Lines

| 2-θ° | d value | Intensity | Intensity % |
|---|---|---|---|
| 6.099 | 14.4802 | 4020 | 100.0 |
| 17.151 | 5.1657 | 2656 | 66.1 |
| 20.749 | 4.2773 | 1176 | 29.3 |
| 24.999 | 3.5590 | 941 | 23.4 |
| 26.253 | 3.3918 | 1464 | 36.4 |

Figure 3:
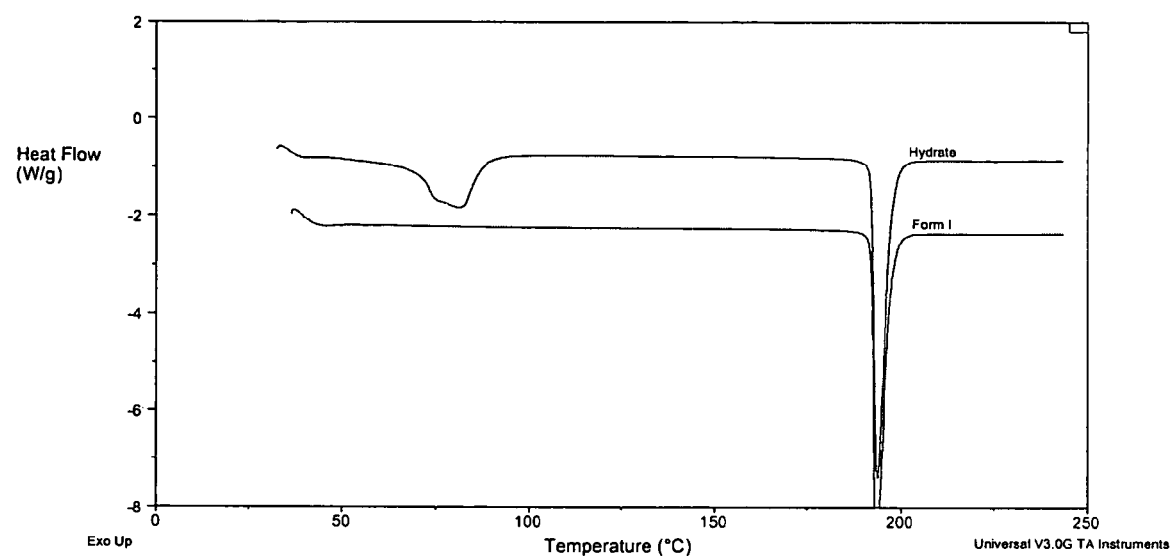
FIG. 3 shows a DSC thermogram of the Compound No. 1 hydrate, as well as a DSC thermogram of polymorph Form I.

In addition, FIG. 3 shows a comparison of DSC endotherms for both the Compound No. 1 hydrate and polymorph Form I. Polymorph Form I is characterized by an endotherm peak at about 193° C. In contrast, the Compound No. 1 hydrate is characterized by a broad endotherm from around 40 to 90° C., which peaks at about 80° C., and an endotherm peak at about 193° C. This broad endotherm is believed to represent the loss of water from the hydrate and the conversion of the Compound No. 1 hydrate to Form I. The second peak at about 193° C. indicates the presence of polymorph Form I.

The Compound No. 1 hydrate may be converted to polymorph Form I under conditions which are reproducible, and that result in polymorph Form I in substantially pure form. As used herein, "substantially pure" means that the polymorph Form I is present in excess of 95% by weight relative to other polymorphic forms of Compound No. 1. Typically, the amount of polymorphs other than polymorph Form I produced according to the present invention is less than the detection limit using DSC, which is about 2% by weight. In other words, in most instances, polymorph Form I is the only detectable form of Compound No. 1 produced by the present invention.

The Compound No. 1 hydrate of this invention may be prepared by dissolving Compound No. 1 in acetic acid to yield an acetic acid solution containing Compound No. 1

("acetic acid solution"), and crystallizing the Compound No. 1 hydrate from the acetic acid solution. This may be accomplished by combining the acetic acid solution with an aqueous solution. The aqueous solution may contain water and one or more optional cosolvents ("aqueous solution"). As used herein, reference to combining the acetic acid solution with the aqueous solution is intended to encompass adding the acetic acid solution to the aqueous solution as well as adding the aqueous solution to the acetic acid solution, unless specified to the contrary. The resulting solids may then be collected, typically by filtration followed by one or more optional washing steps as known to one skilled in the art, to yield the Compound No. 1 hydrate.

In the preparation of the acetic acid solution, Compound No. 1 may be added to acetic acid over a wide concentration range, up to and including its saturation point (or supersaturation point under appropriate conditions). To enhance solubility of Compound No. 1 in acetic acid, the solution may be heated to temperatures ranging from room temperature up to and including its reflux temperature. In one embodiment, the acetic acid solution is heated to a temperature ranging from about 40° C. to reflux. To remove solid particulates, the acetic acid solution may be filtered prior to the crystallization step. Alternatively, and in another embodiment, the reaction mixture of (3-amino-1H-pyrazol-4-yl)-2-thienyl-methanone and N-[3-[3-(dimethylamino)-1-oxo-2-propenyl]-phenyl]-N-methylacetamide in glacial acetic acid may be used as the acetic acid solution.

Compound No. 1 may be obtained by any number of known techniques, including the technique as disclosed in Example 1 below. In that example, Compound No. 1 is synthesized from a mixture of (3-amino-1H-pyrazol-4-yl)-2-thienylmethanone and N-[3-[3-(dimethylamino)-1-oxo-2-propenyl]-phenyl]-N-methylacetamide in glacial acetic acid at elevated temperature. Deionized water is added over several hours at elevated temperature, and a relatively small amount of polymorph Form III of Compound No. 1 is added as a "seed crystal." After cooling, the solids are filtered, washed with water, added to acetone, and then stirred. The solids are then filtered and washed with acetone to give polymorph Form III of Compound No. 1. While this has been found to be a particularly advantageous route for synthesis of large quantities of Compound No. 1 (as polymorph Form III), other forms of Compound No. 1 may be utilized. For example, any polymorphic form, as well as anhydrous or solvated form, or any mixtures thereof may be utilized.

As mentioned above, the Compound No. 1 hydrate is formed by combining the acetic acid solution with the aqueous solution. In one embodiment, the aqueous solution is water alone—that is, no optional cosolvent is present. In another embodiment, the optional cosolvent is present and selected from an organic solvent that is miscible with water, such as acetone, methanol, ethanol, tetrahydrofuran, 2-propanol, dimethylformamide, and mixtures thereof. Upon combining the acetic acid solution with the aqueous solution (i.e., water alone or a mixture of water and one or more cosolvents), the Compound No. 1 hydrate crystallizes or "crashes out" of solution.

When present, the optional cosolvent(s) of the aqueous solution may range in concentration from about 0.1% up to a maximum of about 50% by volume, generally from about 1% to about 40% by volume, and typically from about 2% to about 30% by volume. In a further specific embodiment, the optional cosolvent(s) when present may range from about 5% to about 10% by volume.

Upon addition of the acetic acid solution to the aqueous solution, the resulting solid precipitate is generally filtered (and optionally washed with, for example, water) to yield the Compound No. 1 hydrate. Conditions such as the addition temperature, the ratio of acetic acid solution to aqueous solution, the amount and choice of optional cosolvents, the stir time, and collection procedures all can have an effect on the formation of the Compound No. 1 hydrate, and may be optimized by one skilled in the art in view of the present invention.

The acetic acid solution may be combined with the aqueous solution at a reduced temperature range. As used herein, a "reduced temperature" is a temperature below about 50° C. Specific examples of reduced temperatures which may be suitable in the present invention include, for example, temperatures of below about 40° C., temperatures below about 30° C., and temperatures ranging from about 0 to about 30° C.

The process of combining the acetic acid solution with the aqueous solution (either via addition of the acetic acid solution to the aqueous solution, or of the aqueous solution to the acetic acid solution) may be performed over a period of time ranging from, for example, 1 to 180 minutes, and largely depends on the ability to maintain the combined solution within a desired reduced temperature range.

Once produced, the Compound No. 1 hydrate may be dried to yield polymorph Form I, preferably in substantially pure form as discussed above. A variety of drying temperatures and/or times may be employed. For example, the Compound No. 1 hydrate may be dried at a temperature ranging from about room temperature up to about 90° C., typically in step fashion over a time period ranging from 2-4 hours to greater than 24 hours. Such drying may be conducted under reduced pressure.

The present invention also includes pharmaceutical compositions containing polymorph Form I prepared according to the present invention. Such pharmaceutical compositions may comprise a pharmaceutically effective amount of polymorph Form I prepared according to the present invention and one or more pharmaceutically acceptable carriers and/or diluents. Typically, the pharmaceutical compositions of the present invention include polymorph Form I in an amount ranging from 0.1 mg to 250 mg per dosage depending upon the route of administration, and more typically from 1 mg to 60 mg, from 5 mg to 30 mg, from 10 mg to 20 mg, or from 15 mg to 20 mg. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain—in addition to polymorph Form I—diluents, dispersing and surface-active agents, binders, lubricants, and/or delayed releases agents. One skilled in this art may further formulate the polymorph in an appropriate manner, and in accordance with accepted practices, such as those disclosed in Remington's Pharmaceutical Sciences, Gennaro, Ed., Mack Publishing Co., Easton, Pa. 1990 (incorporated herein by reference in its entirety).

In another embodiment, the invention provides a method for treating a mammal (e.g., a person) having a condition that is susceptible to treatment by administration of one or more agents, including polymorph Form I, that possess anxiolytic, anti-anoxic, sleep-inducing, hypnotic, anticonvulsant, and/or skeletal muscle relaxant properties. Such conditions include insomnia specifically, as well as sleep disorders generally, and other neurological and psychiatric conditions, anxiety states, and vigilance disorder. Such conditions also may include behavioral disorders attributable to cerebral vascular damage and to the cerebral sclerosis encountered in geriatrics, epileptic vertigo attributable to cranial trauma, and metabolic encephalopathies.

The methods of this invention include systemic administration to a mammal (e.g., a person) of a pharmaceutical composition containing a carrier or diluent and a pharmaceutically effective amount of polymorph Form I prepared according to the present invention. As used herein, systemic administration encompasses both oral and parenteral methods of administration. For oral administration, suitable pharmaceutical compositions include powders, granules, pills, tablets and capsules, as well as liquids, syrups, suspensions and emulsions. These compositions may also include flavorants, preservatives, suspending, thickening and emulsifying agents, and other pharmaceutically acceptable additives. Suitable parenteral pharmaceutical compositions include aqueous solutions which may contain buffers, antioxidants, bacteriostats and/or other additives commonly employed in such solutions.

The following examples are offered by way of illustration, not limitation.

EXAMPLE 1

Preparation of Acetic Acid Solution Containing Compound No. 1

A mixture of (3-amino-1H-pyrazol-4-yl)-2-thienylmethanone (36.0 kg) and N-[3-[3-(dimethylamino)-1-oxo-2-propenyl]-phenyl]-N-methylacetamide (45.9 kg) in glacial acetic acid (275 L) was heated at 81-86° C. for 5 hours. Deionized water (360 L) was added over 2 hours maintaining the temperature from 82 to 86° C. Approximately 0.1 kg of polymorph Form III of Compound No. 1 in water (0.7 L) was added as a "seed crystal" and another 288 L of water was added maintaining the temperature from 80-85° C. The reaction mixture was cooled to approximately 25-30° C. over 2 hours and was stirred at the same temperature for 1 hour. The solids were filtered and washed with 180 L of water. The solids were added to acetone (198 L) and were stirred for an hour. The solids were then filtered and washed with acetone to give polymorph Form III of Compound No. 1. The resulting Compound No. 1 (as polymorph Form III) was then added to acetic acid (288 L) and the mixture was heated to approximately 46° C. yielding an acetic acid solution containing Compound No. 1.

EXAMPLE 2

Formation of Compound No. 1 Hydrate

The acetic acid solution containing Compound No. 1 of Example 1 was filtered, cooled to 25° C., and the filtrate added over 2 hours to a solution of water (648 L) and acetone (36 L) (i.e., approximately 5% by volume acetone) at 22° C. After the addition was complete, the reaction mixture was stirred for 1 hour and the solid was collected by filtration. The solid was washed with water (180 L) to give the Compound No. 1 hydrate.

EXAMPLE 3

Conversion of Compound No. 1 Hydrate to Polymorph Form I

The Compound No. 1 hydrate of Example 2 was dried for approximately 2 days at temperatures ranging from 22° C. to 90° C. (i.e., 21 hours at 22° C. to 32° C., followed by 23 hours at 90° C.) to yield 59.2 kg of polymorph Form I of Compound No. 1 (no other polymorphic form(s) were detected by DSC).

EXAMPLE 4

Formation of Acetic Acid Solution Containing Compound No. 1

In Example 2 above, the filtrate (an acetic acid solution containing Compound No. 1) was added to an aqueous solution containing about 5% by volume of acetone at 22° C. This solution was then stirred and the resulting solids collected to give the Compound No. 1 hydrate. In Examples 5-11 below, about 20 g of Compound No. 1 was first dissolved in 100 mL of acetic acid (referred to below as "the acetic acid solution"), added to an aqueous solution under various conditions to generate the Compound No. 1 hydrate, and then the Compound No. 1 hydrate dried to yield the final polymorph Form I product.

EXAMPLE 5

Cosolvent Concentration

In a series of experiments, the acetic acid solution of Example 4 was added to a mixture of 0.1 g of polymorph Form I of Compound No. 1 and 220 mL total volume of deionized water and acetone, at a volume ratio ranging from 0-50% acetone, while maintaining the temperature at 20° C. to 25° C. The resulting mixtures were stirred for 1 hour at 20° C. to 25° C. and then filtered. The filter cakes were washed with water twice and then dried at 50° C. These tests showed that increasing the amount of acetone from 0 to 50% by volume negatively impacted the isolated yield of polymorph Form I and, at high concentrations of acetone, gave predominantly polymorph Form III.

EXAMPLE 6

Mixing Temperature

The acetic acid solution of Example 4 was added to a mixture of 0.1 g of polymorph Form I and 200 mL of deionized water and 20 mL of acetone (i.e., approximately 10% by volume acetone), while maintaining the temperature within a predefined temperature range during the addition, the 1 hour stirring and filtration steps. The resulting filter cakes were then washed with water twice and dried at 50° C.

In a series of experiments, the temperature range during which the addition and stirring steps were performed ranged from 0° C. up to 50° C. It was found that the overall recovery of polymorph Form I was higher at lower temperatures within this range, and that the product isolated increasingly became a mixture of polymorphs of Compound No. 1 at the higher temperatures tested.

EXAMPLE 7

Rates of Addition

In a series of experiments, the acetic acid solution of Example 4 was added, over a predefined time period of from 5 to 180 minutes, to a mixture of 0.1 g of polymorph Form I of Compound No. 1 and 220 mL total of deionized water and acetone, while maintaining the temperature at approximately 25° C. during the addition, the 1 hour stirring and filtration steps. The filter cake was washed with water twice and then was dried at 50° C.

At acetone amounts varying from 0 to 40 mL, addition rates of 5 minutes generally resulted in mixtures of polymorphs, while additions over approximately 3 hours sometimes resulted in a mix of polymorphs. Intermediary addition times between 5 minutes and 3 hours gave the Compound No. 1 hydrate which, upon subsequent drying, yielded pure polymorph From I. Also, there was little difference in yield of product from the slow to the fast addition rates at a given cosolvent concentration.

EXAMPLE 8

Stir Times

In a series of experiments, the acetic acid solution of Example 4 was added to a mixture of 0.1 g of polymorph Form I and 220 mL total of deionized water and acetone, while maintaining the temperature at approximately 25° C. during the addition, the variable stirring and filtration steps. The filter cake was washed with water twice and then dried at 50° C.

At acetone amounts varying from 0 to 40 mL, and stir times varying from 1 hour to overnight, pure polymorph Form I was obtained. The only exception being that mixtures of polymorphs were obtained under conditions where the suspension was stirred for longer periods of time (e.g., longer than 5 hours) in aqueous solutions containing 40 mL of acetone.

EXAMPLE 9

Cosolvents

In a series of experiments, the acetic acid solution of Example 4 was added to a mixture of 0.1 g of polymorph Form I and 220 mL total of deionized water and a cosolvent, while maintaining the temperature at approximately 25° C. during the addition, the 1 hour stirring and filtration steps. The filter cake was washed with water twice and then was dried at 50° C.

Cosolvents other than acetone (i.e., methanol, ethanol, tetrahydrofuran, 2-propanol and dimethylformamide) at 20 mL in 200 mL of water resulted in a Compound No. 1 hydrate that, upon subsequent drying, yielded polymorph Form I. In contrast, at 40 mL of cosolvent and 180 mL of water, lower yields were observed than with the above 20 mL experiments. The 40 mL methanol experiment resulted in a mixture of polymorphs.

EXAMPLE 10

Drying Temperatures

Sealed vials containing approximately 2 g of Compound No. 1 crystallized by the addition of the acetic acid solution of Example 4 to a 10/1 volume mix of water/acetone were prepared and placed in an oven. Individual vials were heated at temperatures ranging from 30 to 90° C., and the crystalline form was monitored by DSC. At temperatures below 60° C., polymorph Form I was observed. In contrast, at temperatures of 60° C. and above, a mixture of polymorphs of Compound No. 1 was observed. Sealed vials of Compound No. 1 crystallized by the addition of the acetic acid solution to water containing no cosolvent showed similar results.

EXAMPLE 11

Addition of Water to Acetic Acid Solution

Water (200 mL) was added to the acetic acid solution of Example 4, while maintaining the temperature below 30° C. The resulting solid was collected by filtration, washed with water, collected and dried, resulting in polymorph Form I.

EXAMPLE 12

Amount of Acetic Acid

Approximately 20 g of Compound 1 was dissolved in acetic acid and the resulting solution was added over 30 minutes to a stirred mixture of water (200 mL), acetone (20 mL) and seed crystals of polymorph Form I at approximately 25° C. After stirring for an hour at the same temperature, the resulting solid was collected by filtration, washed with water and dried at 50° C.

In a series of experiments, the amount of acetic acid used to dissolve the Compound 1 was varied from 40 to 100 mL. Pure polymorph Form I was observed when greater amounts of acetic acid were used while a mixture of polymorphs was found when smaller amounts of acetic acid were employed.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A method for making polymorph Form I of N-methyl-N-(3-{3-[2-thienylcarbonyl]-pyrazol-[1,5-α]-pyrimidin-7-yl}phenyl)-acetamide, comprising drying a hydrate of N-methyl-N-(3-{3-[2-thienylcarbonyl]-pyrazol-[1,5-α]-pyrimidin-7-yl}phenyl)-acetamide.

2. The method for making polymorph Form I of N-methyl-N-(3-{3-[2-thienylcarbonyl]-pyrazol-[1,5-α]-pyrimidin-7-yl}phenyl)-acetamide according to claim 1, wherein the hydrate has a broad endotherm at about 40° C.-90° C. and an endotherm peak at about 193° C. as measured by Differential Scanning Calorimeter at a scan rate of 10° C. per minute.

3. A method for making polymorph Form I of N-methyl-N-(3-{3-[2-thienylcarbonyl]-pyrazol-[1,5-α]-pyrimidin-7-yl}phenyl)-acetamide, comprising drying a hydrate of N-methyl-N-(3-{3-[2-thienylcarbonyl]-pyrazol-[1,5-α]-pyrimidin-7-yl}phenyl)-acetamide having an X-ray powder diffraction pattern having characteristic peaks expressed in degrees 2θx+/− 0.2°θ at 6.1 and 17.2.

4. The method for making polymorph Form I of N-methyl-N-(3-{3-[2-thienylcarbonyl]-pyrazol-[1,5-α]-pyrimidin-7-yl}phenyl)-acetamide according to claim 3, wherein said hydrate further comprises an X-ray powder diffraction pattern peak at 26.3.

5. A method for making a hydrate of N-methyl-N-(3-{3-[2-thienylcarbonyl]-pyrazol-[1,5-α]-pyrimidin-7-yl}phenyl)-acetamide comprising:

combining an acetic acid solution comprising N-methyl-N-(3-{3-[2-thienylcarbonyl]-pyrazol-[1,5-α]-pyrimidin-7-yl}phenyl)-acetamide and acetic acid with an aqueous solution comprising water and one or more optional cosolvents to form a hydrate of N-methyl-N-(3-{3-[2-thienylcarbonyl]-pyrazol-[1,5-α]-pyrimidin-7-yl}phenyl)-acetamide.

6. The method of claim 5 wherein the cosolvent is acetone, methanol, ethanol, tetrahydrofuran, 2-propanol, or dimethylformamide.

7. The method of claim 6 wherein said cosolvent is acetone.

8. The method of claim 5 wherein the acetic acid solution is heated to a maximum temperature of between 40° C. and reflux prior to combining the acetic acid solution with the aqueous solution.

9. The method of claim 5 wherein said N-methyl-N-(3-{3-[2-thienylcarbonyl]-pyrazol-[1,5-α]-pyrimidin-7-yl}phenyl)-acetamide is synthesized in acetic acid to provide the acetic acid solution.

10. The method of claim 1 wherein drying comprises heating the hydrate.

* * * * *